United States Patent
Sasaki

(10) Patent No.: US 8,403,854 B2
(45) Date of Patent: Mar. 26, 2013

(54) ULTRASOUND DIAGNOSIS APPARATUS AND METHOD FOR ACQUIRING 3-D IMAGES

(75) Inventor: Takuya Sasaki, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1141 days.

(21) Appl. No.: 12/196,068

(22) Filed: Aug. 21, 2008

(65) Prior Publication Data

US 2009/0054776 A1 Feb. 26, 2009

(30) Foreign Application Priority Data

Aug. 21, 2007 (JP) ................................. 2007-214502

(51) Int. Cl.
*A61B 8/00* (2006.01)
(52) U.S. Cl. ........ 600/443; 600/407; 600/437; 600/444; 600/445; 600/446
(58) Field of Classification Search .................. 600/407, 600/437, 443–449; 382/128
See application file for complete search history.

(56) References Cited

U.S. PATENT DOCUMENTS

| | | | | |
|---|---|---|---|---|
| 5,159,931 A | * | 11/1992 | Pini | ............................... 600/443 |
| 5,754,618 A | * | 5/1998 | Okamoto et al. | ................. 378/4 |
| 6,464,642 B1 | * | 10/2002 | Kawagishi | ..................... 600/454 |
| 6,544,175 B1 | | 4/2003 | Newman | |

FOREIGN PATENT DOCUMENTS

| | | |
|---|---|---|
| JP | 2006-254985 | 9/2006 |
| JP | 2007-82649 | 4/2007 |

OTHER PUBLICATIONS

Japanese Office Action issued Mar. 27, 2012, in Japan Patent Application No. 2007-214502 (with English translation).

* cited by examiner

*Primary Examiner* — Tse Chen
*Assistant Examiner* — Joel F Brutus
(74) *Attorney, Agent, or Firm* — Oblon, Spivak, McClelland, Maier & Neustadt, L.L.P.

(57) ABSTRACT

An ultrasound diagnosis apparatus and a 3-D image data scan method that can continuously display 3-D image data in both a pre-scan mode and a triggered entire volume mode by collecting the volume data of a plurality of volume scan regions of an object from the start of the scan. In the pre-scan mode, a plurality of 3-D sub-regions are set by dividing an object scan region along a direction vertical to the reference scan plane. In a triggered volume mode for collecting volume data, a 3-D scan of a 3-D sub-region including the reference scan plane is performed in preference to other 3-D sub-regions in order to continuously display 2-D image data acquired on the reference scan plane in the pre-scan mode and MPR image data acquired in the entire triggered volume mode from an initial scan time.

7 Claims, 11 Drawing Sheets

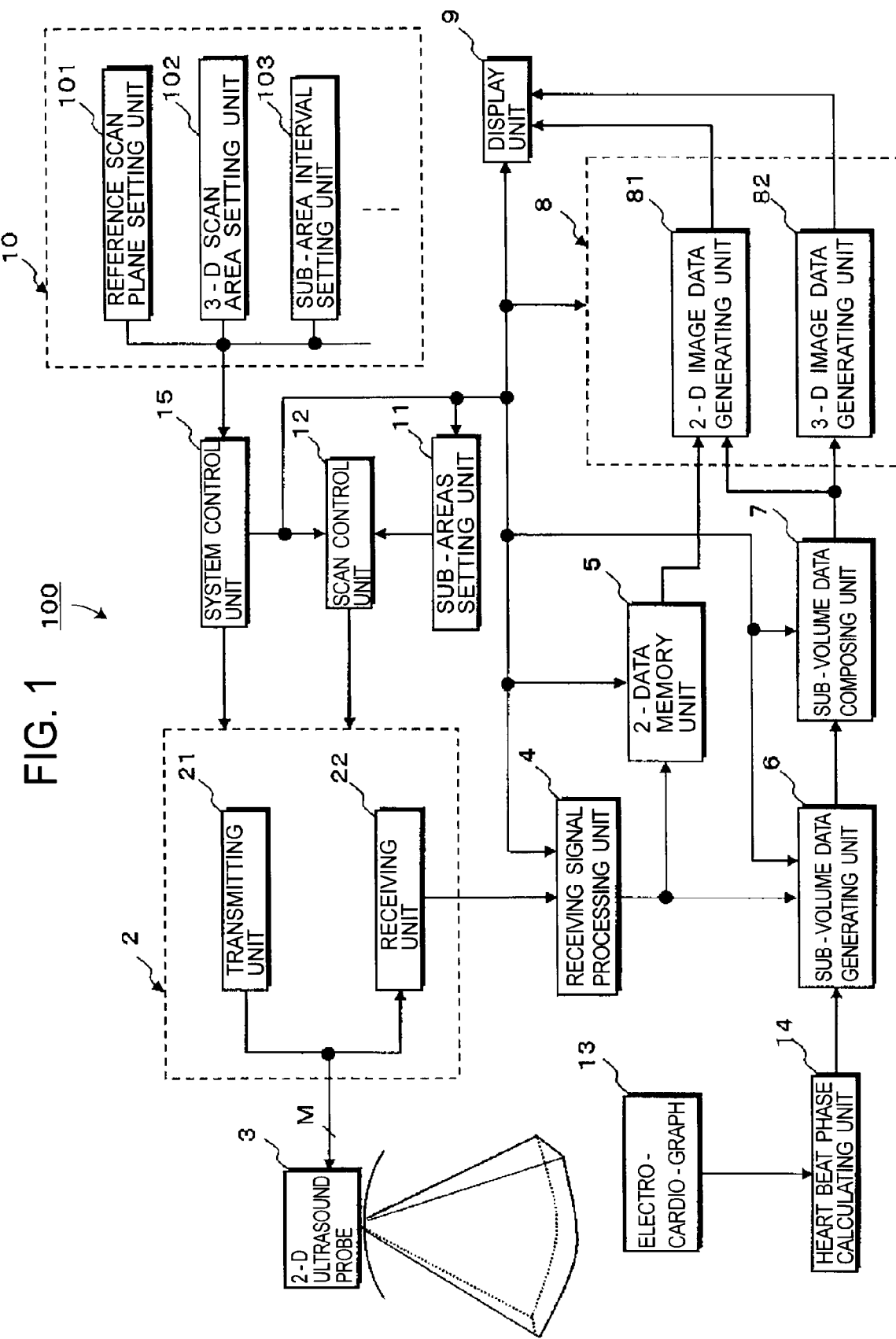

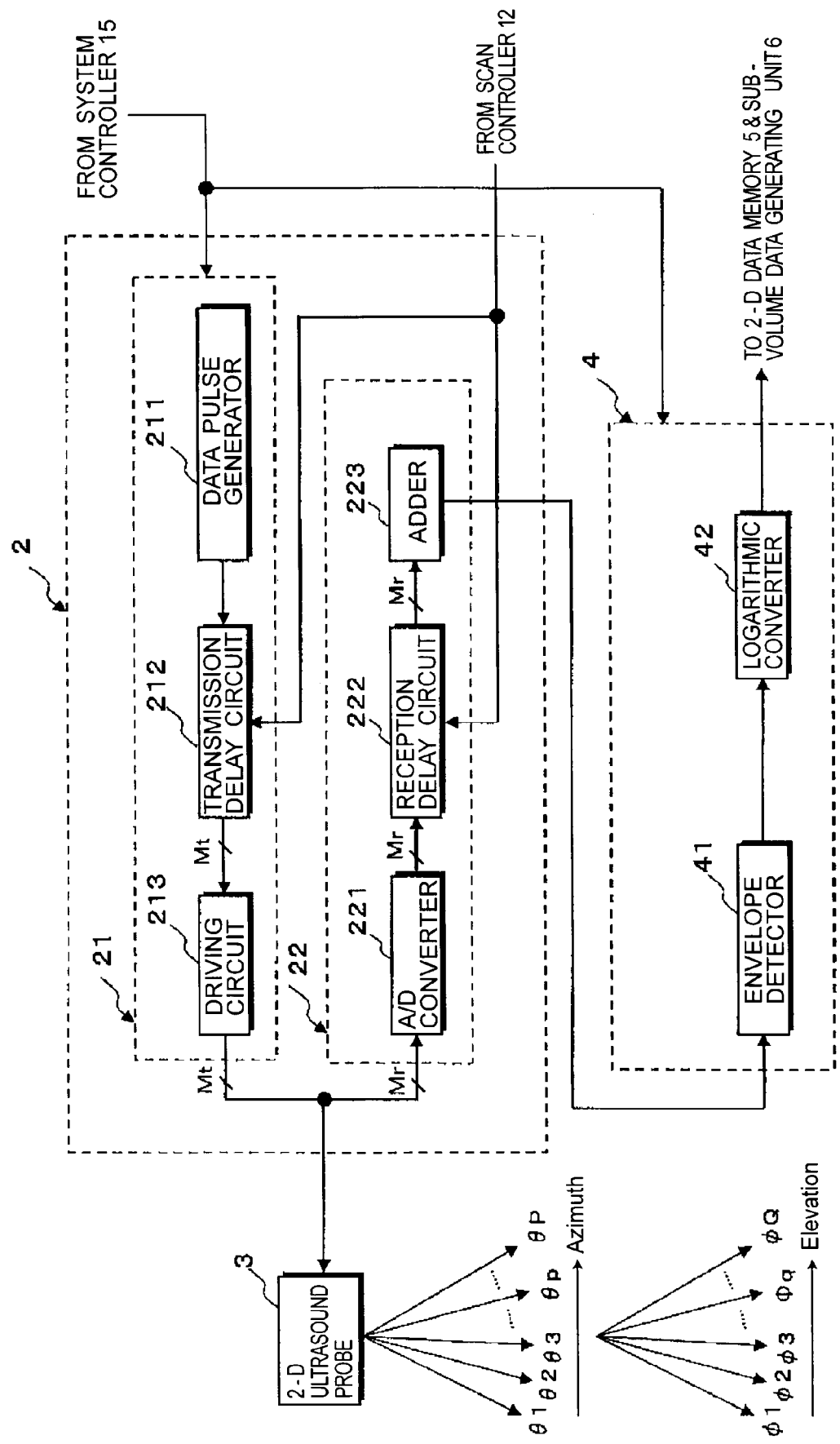

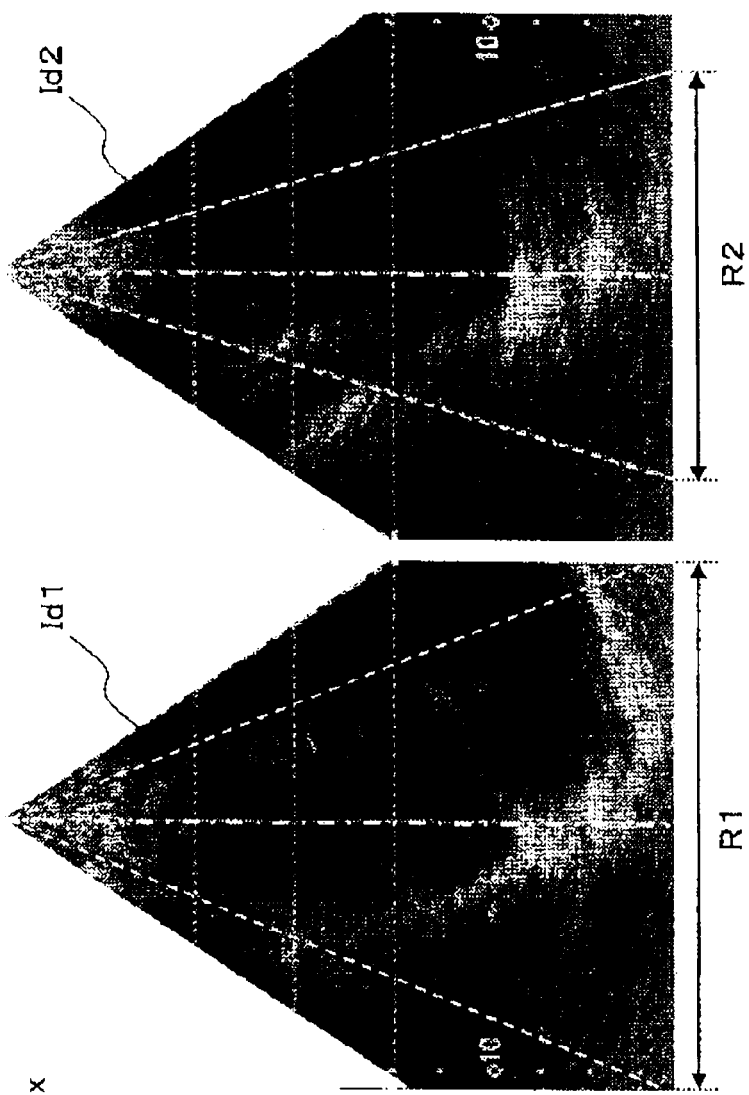

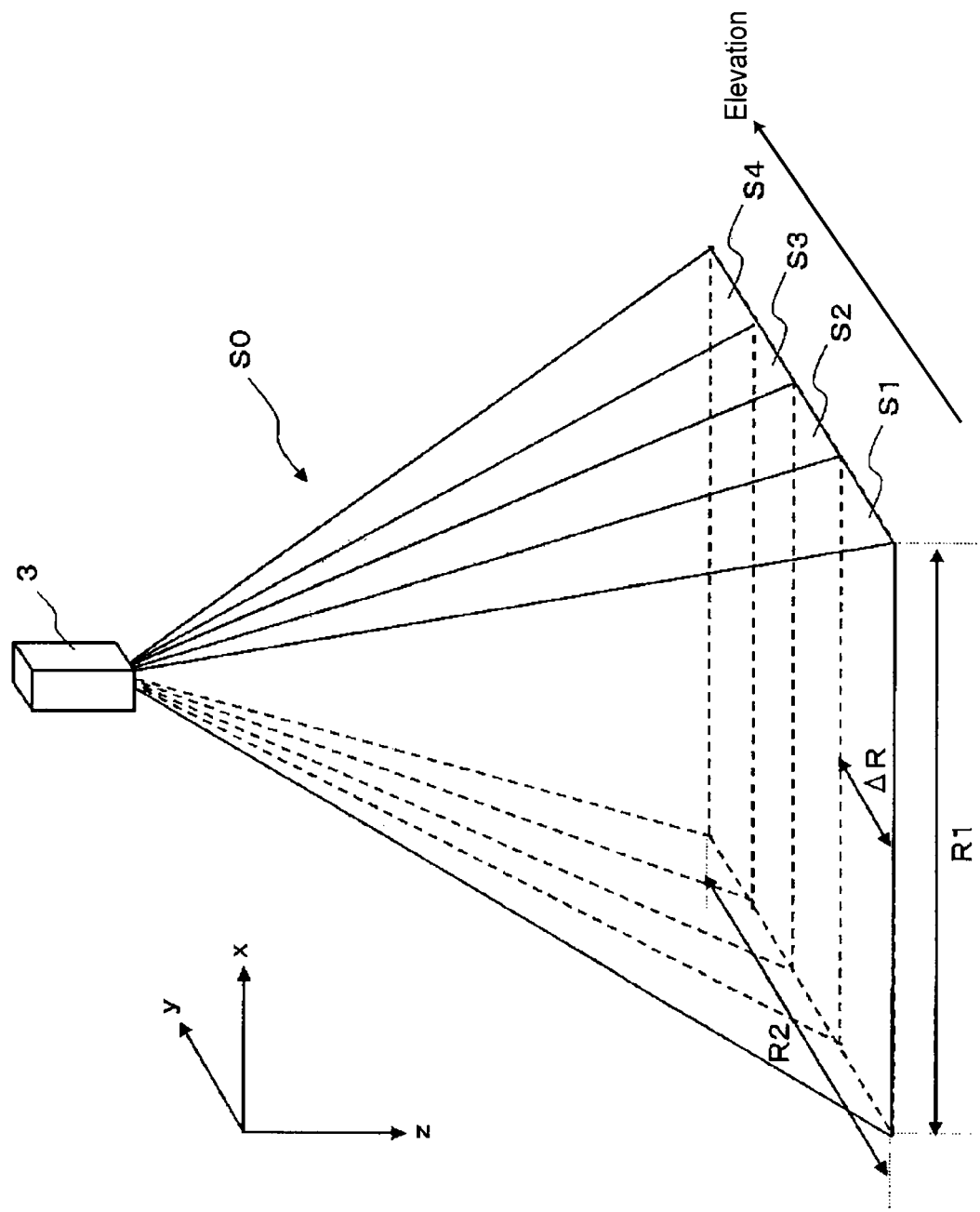

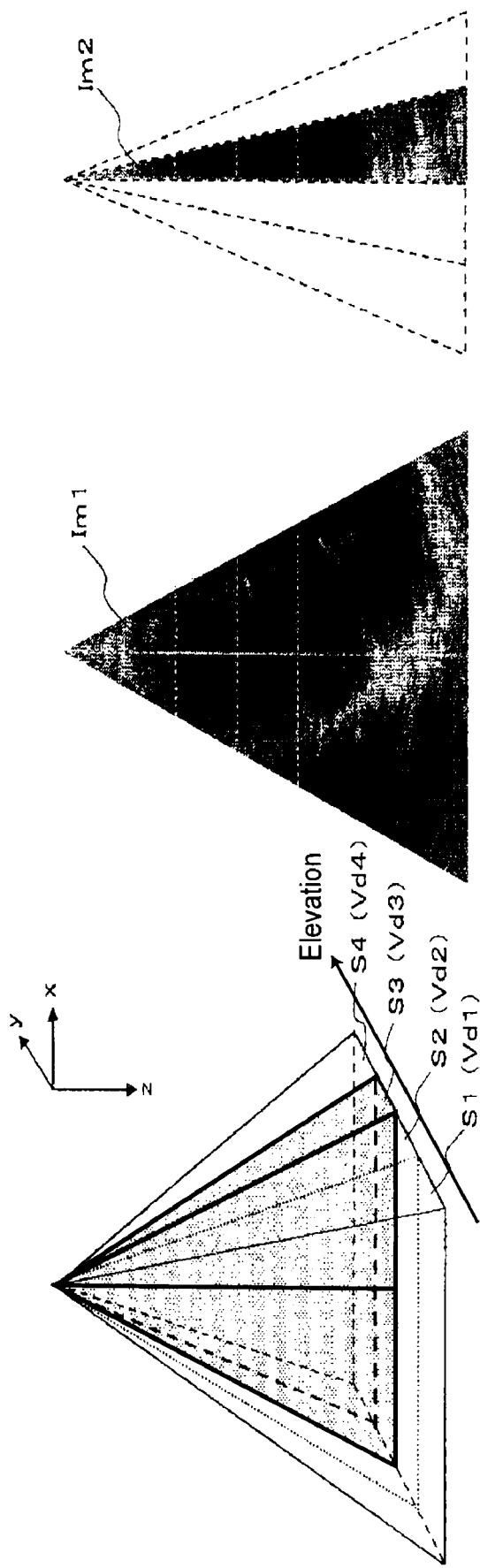

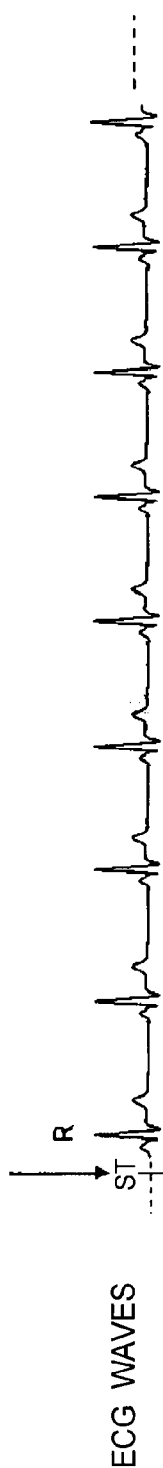

1st H.B.PERIOD[t0-t1]

2nd H.B.PERIOD[t1-t2]

3rd H.B.PERIOD[t2-t3]

4th H.B.PERIOD[t3-t4]

ULTRASOUND DIAGNOSIS APPARATUS AND METHOD FOR ACQUIRING 3-D IMAGES

CROSS-REFERENCE TO RELATED APPLICATIONS

This application claims priority from, and the benefit of, Japanese Patent Application No. 2007-214502, filed on Aug. 21, 2007, the contents of which are expressly incorporated herein by reference in their entirety.

BACKGROUND OF THE INVENTION

A. Field of the Invention

The present invention relates to an apparatus for acquiring and displaying 3 dimensional (3-D) image data by scanning a plurality of sub-regions of a target scan region and a method for acquiring and displaying ultrasound 3-D images. More particularly, the present invention relates to an ultrasound diagnosis apparatus that can set a 3-D scan target region in a preliminary scan mode (hereinafter, "pre-scan mode") and acquire 3-D image data (hereinafter, "volume data") by sequentially scanning a plurality of sub-divided scan regions (hereinafter, "sub-scan region") of the target region and a method for acquiring volume data of the target region by initially scanning a sub-scan region that contains or borders a reference plane of the pre-scan mode, or the closest sub-scan area.

B. Background of the Invention

An ultrasound image diagnosis apparatus transmits and receives ultrasound through a plurality of ultrasound transducers installed in an ultrasound probe to and from a target in an object in a plurality of directions in order to display the image of the target on a monitor. Since an ultrasound image diagnosis apparatus can easily obtain and display a two dimensional image or a three dimensional image in real time by simply touching an ultrasound probe to a patient's body surface, it is widely used as an apparatus for diagnosing the status of a target organ in a patient's body.

Conventionally, these devices must move their probes' 1-D array transducers in a direction orthogonal to an array direction or rotate the 1-D array of transducers in order to acquire 3-D image data by using an ultrasound probe having a plurality of transducers arrayed in one dimension (1-D) by transmitting and receiving ultrasound over a 3-D area of a target organ in an object. 3-D image data are generated by rendering the acquired 3-D data (hereinafter, "volume data").

Recently, 2-D array ultrasound probes have been used. The 2-D array ultrasound probe includes a plurality of transducers arrayed in two dimensions (2-D) (i.e., an azimuth direction and an elevation direction). By using a 2-D array ultrasound probe, it becomes possible to electrically control whole operations of transmissions and receptions of ultrasound over a 3-D region of a target in order to significantly shorten volume scan time of the target and improve operability of an ultrasound examination.

However, in ultrasound transmission and reception, it has been necessary to repeat ultrasound transmission and echo reception for extremely long times in order to acquire volume data of a desired 3-D region. The required time for performing a respective ultrasound transmission and reception is determined by the acoustic velocity of the ultrasound transmission into an object and the maximum imaging depth. Accordingly, much time is required to acquire volume data of a sufficient spatial resolution.

To address this problem for real-time display of image data, a technique has been developed to simultaneously receive a plurality of echo ultrasound signals reflected from a target in an object. This is defined as a parallel simultaneous receiving method. By applying the parallel simultaneous receiving method to a 3-D scan (volume scan), it becomes possible to reduce 3-D data acquisition time. However, a very large number of parallel receptions are required in order to perform a volume scan for an organ that moves in accordance with each heart beat or cardiac cycle, such as a patient's heart. To realize such a large number of parallel receptions, very complicated circuit arrangements for ultrasound devices have been required. This is a serious problem for manufacturing in view of cost performance.

To solve the above-mentioned problem, U.S. Pat. No. 6,544,175 has proposed a method for collecting volume data by dividing a portion of a diagnosis subject into a plurality of 3-D sub-regions in order to successively scan the plurality of 3-D sub-regions while synchronizing with a cardiac cycle. Hereinafter, in order to assist a simple understanding of this specification, such a method for acquiring volume data by sequentially scanning a plurality of regions by referencing and synchronizing to ECG (electric cardiogram) signals of a patient's heart beats is simply referred to as a "triggered volume scan" method.

The conventional triggered volume scan method performs a plurality of volume scans sequentially over each of a plurality of 3-D sub-regions of a subject's volume scan region during a prescribed period and stores the acquired sub-volume data with the cardiac cycle data after once displaying the newly acquired sub-volume data. When acquisition of sub-volume data for a plurality of 3-D sub-regions has completed, volume data for each volume scan regions is generated by combining each of the sub-volume data sets of the plurality of 3-D sub-regions at the same heart beat phases. The compounded 3-D image data are processed so as to generate 3-D image data, such as sequential volume rendering image data and multi planar reconstruction (MPR) image data at a desired slice plane. By doing so, it becomes possible to observe 3-D image data of a diagnosis object portion as a motion image.

The conventional triggered volume scan method designates a reference scanning plane and a volume scan region based on 2-D image data acquired by a single plane scan or a multi-plane scan, such as a bi-plane scan over a diagnosis object portion in a pre-scan mode performed before acquiring entire volume data over a volume scan region.

In the entire volume data acquisition mode, the volume scan area is divided into a plurality of 3-D sub-regions based on a prescribed interval between the sub-regions. Each of the plurality of 3-D sub-region is successively scanned in order to collect data for each sub-volume. By composing the collected sub-volume data, 2-D multi planar reconstruction image data (hereinafter "MPR image data") at a reference scanning plane and 3-D image data are generated and displayed in a display unit. By monitoring the displayed MPR image data, it is judged whether acquisition of volume data of a volume scan region is correctly performed. If a problem is found, the acquisition of volume data is repeated.

Generally, the volume scan region of a diagnosis portion in an object is based upon a reference scanning plane in order to monitor the acquisition status of volume data for a volume scan region. Consequently, when an acquisition of sub-volume data of a plurality of 3-D sub-regions is started from a 3-D sub-area located at an edge portion of the volume scan region, it happens to display no MPR image data for the reference scanning plane while collecting sub-volume data of the plurality of 3-D sub-regions including the reference scanning plane. Thus it becomes impossible to display the most important diagnosis data until the acquisition of sub-volume data for the 3-D sub-regions is completed.

Thus, while the triggered volume scan method collects 2-D image data of the reference scanning plane by performing acquisition of 2-D image data with matching positions of two orthogonal cross-sections in the pre-scan mode, no display of MPR image data in the reference scanning plane acquired in the triggered entire volume mode occurs. Consequently, triggered volume scans cannot observe the initial view of a motion image of a diagnostic portion. This is a problem because the monitoring accuracy of the volume data is deteriorated. Furthermore, this increases monitoring burdens for an operator.

SUMMARY OF THE INVENTION

To solve the above-mentioned conventional problems and defects, the present invention provides a new ultrasound diagnosis apparatus for sequentially acquiring 3-D image data (volume data) by scanning a plurality of sub-scan regions of a target area, as well as a method for acquiring a volume data of a target area by determining an initial sub-scan region of the plurality of sub-scan regions. Thus, the present invention provides an ultrasound diagnosis apparatus and method for sequentially acquiring volume data of a volume scan region by performing a heart beat synchronized volume scan of a plurality of 3-D sub-regions of a diagnosis object portion in an object.

According to the ultrasound diagnosis apparatus consistent with the present invention, it becomes possible to continuously display both 2-D image data of a reference scanning plane generated in a pre-scan mode of a volume scan region and MPR image data of the reference scanning plane generated based on volume data acquired from the volume scan region in the heart beat synchronized, entire volume mode.

One aspect of the ultrasound diagnosis system consistent with the present invention is an ultrasound diagnosis apparatus configured to sequentially acquire volume data from a volume scan region by applying a heart beat synchronized volume scan method over a plurality of 3-D sub-regions designated on a diagnosis object portion in an object, the ultrasound diagnosis apparatus including:

a reference scanning plane setting unit configured to set a reference scanning plane to the diagnosis object portion;

a 2-D image data generating unit configured to sequentially generate 2-D image data based on signals received from the reference scanning plane;

sub-region setting units configured to set a plurality of 3-D sub-regions by dividing the volume scan region along a direction not parallel to the reference scan;

an MPR image data generating unit configured to sequentially generate MPR image data based on sub-volume data acquired through sub-volume scans of each of the plurality of 3-D sub-regions;

a scan control unit configured to perform the sub-volume scan of a 3-D sub-region that contains or borders the reference scanning plane, or the closest 3-D sub-region to the reference scanning plane; and a display unit configured to display the 2-D image data and the MPR image data.

Another aspect of the ultrasound diagnosis apparatus consistent with the present invention is an ultrasound diagnosis apparatus configured to collect volume data by scanning a volume scan region of a diagnosis object portion in an object, the ultrasound diagnosis apparatus, including:

a reference scanning plane setting unit configured to a reference scanning plane of the diagnosis object portion;

a 2-D image data generating unit configured to sequentially generate 2-D image data based on signals received through the reference scanning plane;

an MPR image data generating unit configured to sequentially generate MPR image data based on the volume data by a volume scan over the volume scan region;

a scan control unit configured to perform an initial ultrasound scan of a reference scanning plane in the volume scan region; and a display unit configured to display the 2-D image data and the MPR image data.

A further aspect of the present invention is an ultrasound diagnosis scanning method for sequentially acquiring volume data over a volume scan region by applying a heart beat synchronized volume scan method over a plurality of 3-D sub-regions provided on a diagnosis object portion in an object, including:

setting a reference scanning plane for the diagnosis object portion;

sequentially generating 2-D image data based on signals received from the reference scanning plane;

setting a plurality of 3-D sub-regions by dividing the volume scan region in a direction crossing the reference scanning plane;

sequentially generating MPR image data based on sub-volume data acquired by volume scan over the plurality of 3-D sub-regions;

controlling the volume scan so as to perform an initial scan of a 3-D sub-region that contains or borders the reference scanning plane, or the closest 3-D sub-region to the reference scanning plane; and displaying the 2-D image data and the MPR image data.

According to the present invention, it becomes possible to continuously display both 2-D image data of a reference scanning plane generated in a pre-scan mode of a volume scan region, and MPR image data of the reference scanning plane generated based on volume data acquired from the volume scan region in the heart beat synchronized entire volume mode. Consequently, monitoring accuracy can be increased when acquiring volume data of a diagnosis portion in an object and burdens for a monitoring operator can be reduced.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or like parts. In the drawings:

FIG. 1 is a block diagram illustrating an ultrasound diagnosis apparatus in accordance with preferred embodiments of the present invention.

FIG. 2 is a block diagram illustrating the transmission and reception unit, and the receiving signal processing unit in the ultrasound diagnosis apparatus shown in FIG. 1.

FIG. 4A illustrates an exemplary reference scanning plane and an auxiliary scan plane being set in a pre-scan mode of an embodiment.

FIG. 4B is an example display of 2-D image data acquired at the reference scanning plane shown in FIG. 4A.

FIG. 4C is an example display of 2-D image data acquired at the auxiliary scan plane shown in FIG. 4A.

FIG. 5 is an example illustrating a plurality of 3-D sub-regions formed by dividing a volume scan region in this embodiment.

FIG. 6A is an example illustrating a reference scanning plane among the four divided 3-D sub-regions shown in FIG. 5.

FIG. 6B is an exemplary display of a multi planar reconstruction (MPR) image data Im1 generated from the reference scanning plane in the sub-volume data acquired with taking preference as shown in FIG. 6A.

FIG. 6C is an exemplary display of an MPR image data Im2 generated from the auxiliary scan plane in the sub-volume data acquired in initial scans as shown in FIG. 6A.

FIG. 7A shows heart beat periods (cardiac cycles) being set in accordance with an electrocardiogram based on switching timing from a pre-scan mode to a triggered entire volume mode in the present embodiment.

FIG. 7B shows newly collected and stored sub-volume data for each of the cardiac cycles shown in FIG. 7A.

FIG. 7C is an exemplary construction of composed sub-volume data generated by composing collected and stored sub-volume data shown in FIG. 7B and already collected and stored sub-volume data.

DESCRIPTION OF THE EMBODIMENTS

Figure 3A:
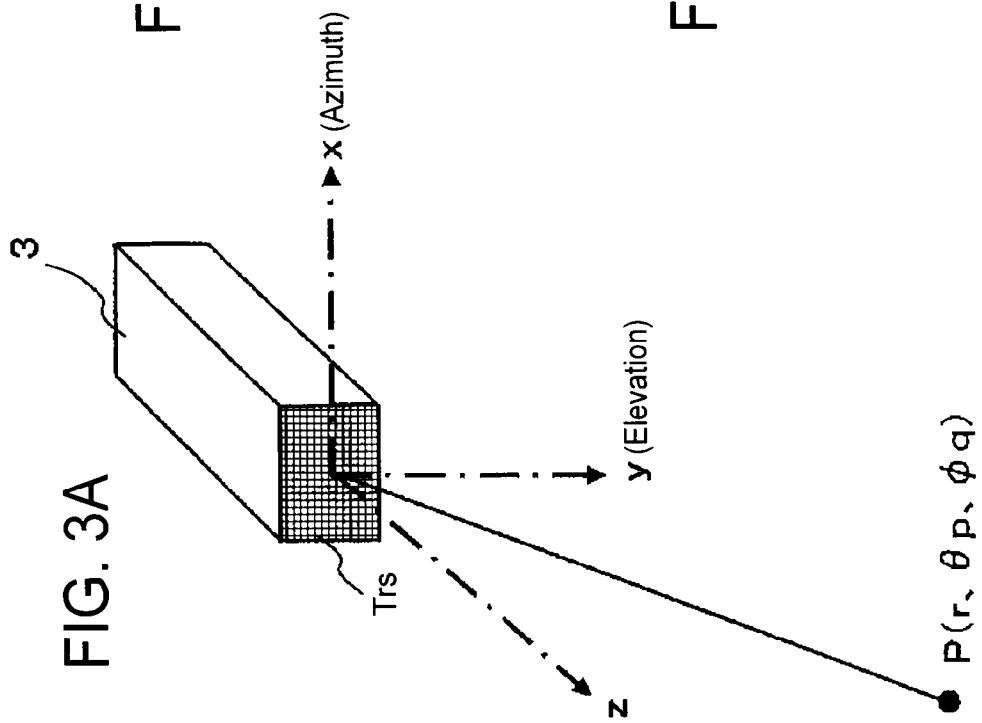
FIG. 3A illustrates the direction of ultrasound transmission and reception in a volume scan by 2-D array transducers provided in an ultrasound probe.

In the following description of the preferred embodiments in accordance with the present invention, prior to the acquisition of 3-D data (volume data) of a diagnosis object portion in an object, a preliminary scan to determine a 3-D data acquiring region (hereinafter, "pre-scan mode") is performed by using two scanning planes orthogonally intersecting with each other (hereinafter, "bi-plane"). Based on the 2-D image data acquired at each of the bi-planes in a pre-scan mode, a volume scan region (scan range) of a particular diagnosis object portion is set and either bi-plane is set as a reference scan plane for acquisition of volume data of the diagnosis object portion.

In the following triggered entire volume mode for acquiring volume data of a target diagnosis portion, the determined volume scan region is divided into a plurality of 3-D sub-regions of the diagnosis object in a direction orthogonal to the reference scan plane at a prescribed interval. According to the present invention, in a triggered entire volume mode for sequentially acquiring volume data of a target region, a particular 3-D sub-region that includes the reference scan plane is initially scanned to acquire sub-volume data among the plurality of the divided 3-D sub-regions. The initial sub-volume data are stored with heart beat (cardiac cycle) phase data. From the initial sub-volume data, two sets of multi-planar reconstruction (MPR) image data are generated by extracting voxels, each corresponding to the reference scan plane and an auxiliary scan plane that orthogonally intersects the reference scan plane. The two generated MPR image data sets are displayed on a display unit in real-time.

Similarly, sub-volume data are serially acquired from a 3-D sub-region adjoining the initial 3-D sub-region included in the reference scan plane and stored with cardiac cycle data. The acquired sub-volume data of the adjoining 3-D sub-region are combined with the previously stored sub-volume data based on the stored cardiac cycle data. By generating MPR image data of the compounded sub-volume data at the reference scan plane and the auxiliary scan plane, the previously displayed MPR image data are renewed by the newly generated MPR image data. Successively, sub-volume data are serially acquired from the remaining sub-regions and MPR image data are also generated based on the stored cardiac cycle data by composing the previous sub-volume data. By monitoring this MPR image data, the acquisition status of volume data of the target region is judged in the triggered entire volume mode.

In this embodiment, for purposes of discussion herein, MPR image data in a triggered entire volume mode are generated and displayed based on a reference scan plane and an auxiliary scan plane, set in a pre-scan mode and orthogonally intersecting the reference scan plane. Of course, it is possible to choose an arbitrary intersection angle with the reference scan plane and the auxiliary scan plane. Usually, either one of the reference scan plane or the auxiliary scan plane is determined as the array direction of a plurality of transducers in an ultrasound probe, as explained later.

FIG. 1 is a block diagram of an ultrasound diagnosis system 100 in accordance with preferred embodiments of the present invention. The ultrasound diagnosis system 100 includes a transmission/reception unit 2, a 2-D ultrasound probe 3, a receiving signal processing unit 4, a 2-D data memory unit 5, a sub-volume data generating unit 6, a sub-volume data composing unit 7 and a image data generating unit 8. The transmission/reception unit 2 includes a transmitting unit 21 for supplying driving signals to the transducers in the ultrasound probe 3 and a receiving unit 22 for adding receiving signals supplied from the transducers. The ultrasound probe 3 includes a plurality of 2-D arrayed transducers for transmitting ultrasound pulses (transmission ultrasound) over a 2-D area or 3-D volume of a diagnosis object portion in an object in accordance with driving signals from the transmission unit 21 and also for converting ultrasound echo signals into electric signals. The receiving signals acquired from a plurality (M) of channels of the transducers in the ultrasound probe 3 are arranged in phases and added in the receiving unit 22. The added receiving signals are processed for generating B mode image data in the receiving signal processing unit 4.

The 2-D data memory unit 5 stores B mode data collected from an object in a reference scanning plane and an auxiliary scan plane orthogonally intersecting the reference scanning plane during a pre-scan mode before scanning an entire 3-D volume. The collected and processed B mode data are stored so as to correspond to the ultrasound transmission and reception directions.

In a triggered entire volume scan mode, the sub-volume data generating unit 6 generates sub-volume data by storing B mode data acquired from a plurality of 3-D sub-regions that are set up against a 3-D scan region of an object through a sub-region setting unit 11 with cardiac cycle data so as to correspond to transmission and reception directions.

The sub-volume data composing unit 7 composes sub-volume data generated in the sub-volume data generating unit 6 based on the cardiac cycle phase data and sub-region data stored as additional data. The image data generating unit 8 generates 2-D image data and MPR image data of a diagnosis object portion at a reference scan plane and an auxiliary scan plane and 3-D image data of the volume scan region in a diagnosis object portion based on 2-D data supplied from the 2-D data memory unit 5 and composed sub-volume data supplied from the sub-volume data composing unit 7.

The ultrasound diagnosis apparatus 100, as illustrated in FIG. 1, further includes a display unit 9, an input unit 10, a sub-region setting unit 11, a scan control unit 12, a vital signals (electro-cardio graph) measuring unit 13, a heart beat (cardiac cycle) phase calculating unit 14 and a system control unit 15.

The display unit 9 displays 2-D image data and 3-D image data generated by the image data generating unit 8. The input unit 10 performs input operations upon object data, setting image data generating conditions, setting a reference scan plane, setting a volume scan region, setting a sub-region interval (space) in a 3-D sub-region, and so on.

The sub-region setting unit 11 sets up a plurality of 3-D sub-regions by dividing a volume scan region of a diagnosis object portion along a direction orthogonally intersecting a reference scan plane based on volume scan region data and sub-region interval data supplied from the input unit 10. The scan control unit 12 controls delaying times for the transmission and reception unit 2 in order to perform 2-D scans at a reference scan plane and an auxiliary scan plane set on a diagnosis object portion in a pre-scan mode, and also to perform volume scans of a plurality of 3-D sub-regions set on a diagnosis object portion in a triggered entire volume mode. The electro-cardio graph (living body signal measuring) unit 13 measures ECG waves of the object. The heart beat (cardiac cycle) phase calculating unit 14 calculates cardiac cycle phases based on ECG waves provided from the electro-cardio graph measuring unit 13. The system control unit 15 controls all of the above-mentioned units.

The ultrasound probe 3 includes a plurality (M) of 2-D arrayed transducers provided on a top surface portion of the probe. Ultrasound transmission and reception of echo ultrasound are performed by touching the top surface portion to a body surface of an object. Often, a gel is used as an intermediary between the body surface and probe surface. The transducers convert driving pulse signals to transmission signals composed of ultrasound pulses during transmission time, and convert ultrasound echoes to receiving signals during reception time. Each of the plurality M of transducers is coupled to the transmission and reception unit 2 through a multi-channel cable.

In the ultrasound diagnosis system 100 in accordance with preferred embodiments of the present invention, as an example of the ultrasound probe 3, a 2-D array sector scan ultrasound probe including a plurality of M transducers is used. Of course, it is also possible to use, for example, a linear scan ultrasound probe or a convex scan ultrasound probe.

FIG. 2 is a block diagram illustrating the transmission and reception unit, and the receiving signal processing unit in the ultrasound diagnosis apparatus shown in FIG. 1. The transmission unit 21 for supplying drive signals to the transducers in the ultrasound probe 3 includes a rate pulse generator 211, a transmission delay circuit 212 and a driving circuit 213. The rate pulse generator 211 generates rate pulses which determine a recycle period for transmission ultrasound. The generated rate pulses are supplied to the transmission delay circuit 212. The transmission delay circuit 212 includes a plurality of independent delay circuits of the same number of transducers M as used for transmission in order to drive a selected number Mt (Mt is equal or smaller than M) among 2-D array transducers of a total number of M. The transmission delay circuit 212 gives a convergence delay time for converging the transmission ultrasound into a prescribed depth and a deviation delay time for transmitting ultrasound in a prescribed direction ($\theta p$, $\phi q$) to the rate pulses and supplies to the driving circuit 213. The delay time of the transmission delay circuit 212 is controlled by the scan control unit 12.

The reception unit 22 also includes a plurality of independent driving circuits of the same number M as the transmission delay circuit 212. The reception unit 22 includes a plurality of A/D converters 221 and reception delay circuits 222 for selecting Mr transducers (Mr is equal or smaller than M) for reception channels among the 2-D array transducers of number M. The reception unit 22 further includes an adder 223 of 1 channel. The reception signals of Mr channel supplied from the Mr receiving transducers are converted to digital signals in the A/D converter 221 and supplied to the reception delay circuit 222.

The reception delay circuit 222 gives each of the reception signals of Mr channels outputted from the A/D converter 221 a convergence delay time for converging reception ultrasound from a prescribed depth and a deviation delay time for setting a reception directivity to a predetermined direction ($\theta p$, $\phi q$). The reception signals acquired from the prescribed direction ($\theta p$, $\phi q$) are added in the adder 223. The delay time of the reception delay circuit 222 is controlled by the scan control unit 12.

It is possible for the reception unit 22 to simultaneously receive reception ultrasound beams from a plurality of directions by controlling the reception delay circuit 222 of Mr channels supplied from the transducers. By applying this parallel simultaneous reception, it becomes possible to significantly decrease the necessary time for performing a triggered entire volume mode.

The reception signals received by the reception unit 22 are processed and generated as B mode data in the reception signals processing unit 4. The reception signals processing unit 4 includes an envelope detector 41 for detecting the envelope of the reception signals supplied from the adder 223 in the reception unit 22 and a logarithmic converter 42 for generating B mode data by converting the amplitude of the envelope detected reception signals. It is possible to replace of the positions of the envelope detector 41 and the logarithmic converter 42.

The B mode data generated in the reception signals processing unit 4 are supplied to the 2-D data memory unit 5 and the sub-volume data generating unit 6. The system control unit 15 controls both the transmission unit 21 and the reception signals processing unit 4.

Figure 3B:
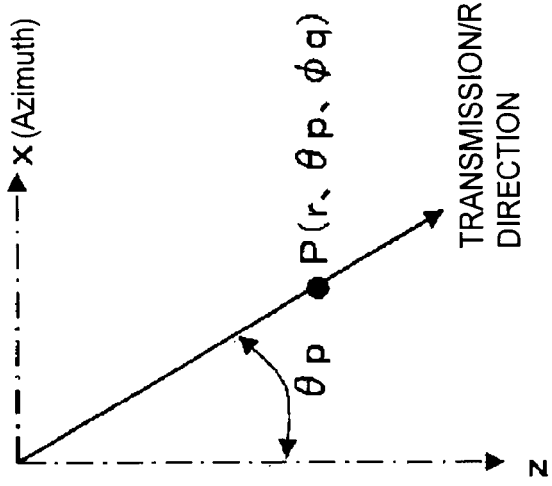
FIG. 3B illustrates the direction of ultrasound transmission and reception projected on the x-z plane in the volume scan shown in FIG. 3A.
Figure 3C:
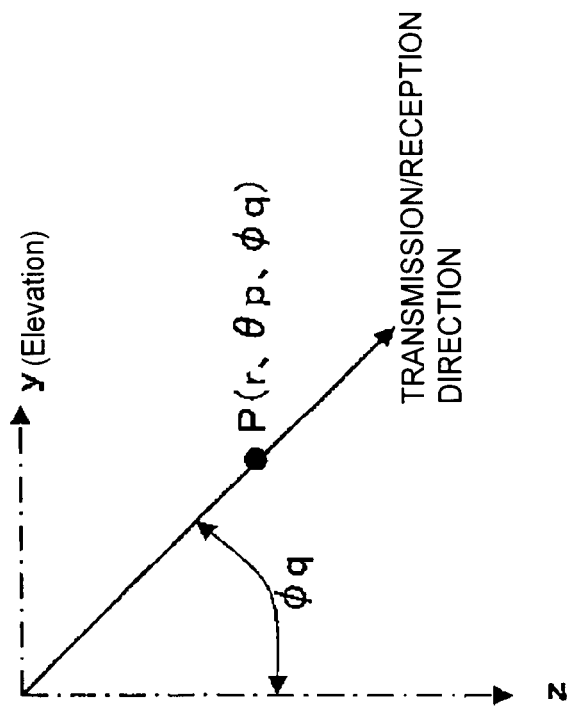
FIG. 3C illustrates the direction of ultrasound transmission and reception projected on the y-z plane in the volume scan shown in FIG. 3A.
Figure 8A:
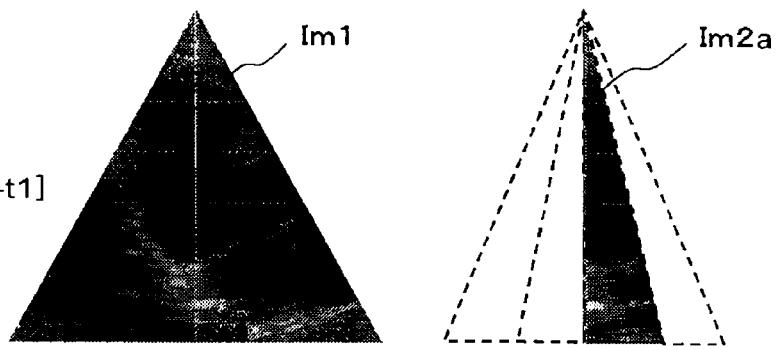
FIGS. 8A-8D are exemplary displays of MPR image data of the reference scanning plane and the auxiliary scan plane displayed in each of cardiac cycles in the embodiment shown in FIG. 7A.
Figure 8B:
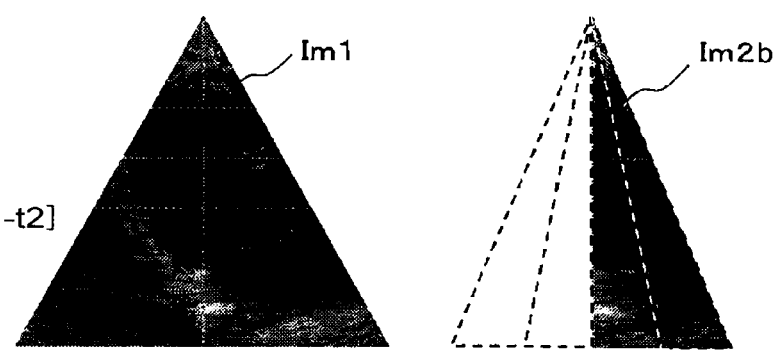
Figure 8C:
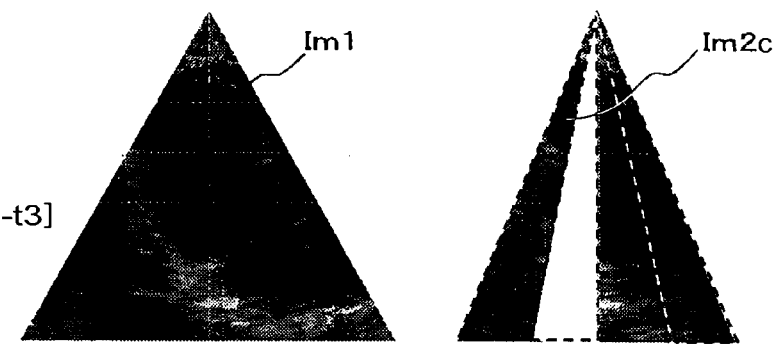
Figure 8D:
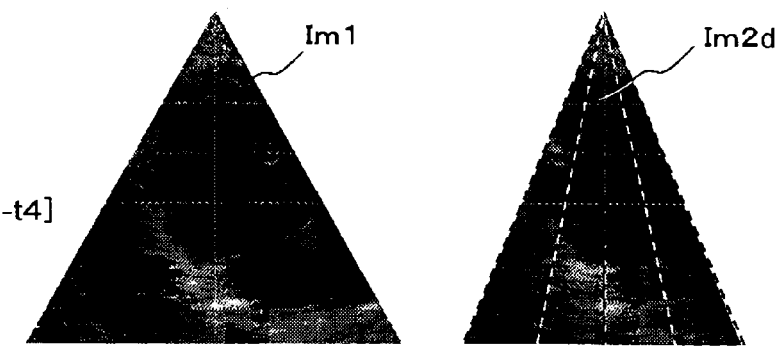

FIG. 3A illustrates an ultrasound probe 3 having 2-D array transducers Trs and an ultrasound transmission/reception position P (r, $\theta p$, $\phi q$). The ultrasound probe 3 has a center axis (z-axis). The ultrasound transmission/reception position P (r, θp, φq) locates at a distance r from a surface of the transducers Trs in an x-axis (azimuth) direction and a y-axis (elevation) direction. FIG. 3B illustrates a projected position P on an x-z plane transmitting and receiving ultrasound at an angle θp in the x-axis (azimuth) direction from the z-axis. FIG. 3C illustrates a projected position P on a y-z plane transmitting and receiving ultrasound at an angle φq in the y-axis (elevation) direction from the z-axis. The delay time in the transmission delay circuit 212 in the transmission unit 21 and the reception delay circuit 222 in the reception unit 22 are controlled by the scan control signals supplied from the scan control unit 12 in order to perform 2-D scan on a reference scan plane and an auxiliary scan plane in a pre-scan mode and perform a volume scan on a 3-D region in a triggered entire volume mode. For instance, a reference scan plane is set on the x-z plane and an auxiliary scan plane is set on the y-z plane.

With reference to FIG. 1, B mode data acquired by 2-D scanning on a reference scan plane and an auxiliary scan plane set in a pre-scan mode is stored in the 2-D data memory unit 5 together with the ultrasound transmission and reception direction data. In this embodiment, positions and directions of the ultrasound probe 3 touching to a body surface of an object are adjusted so as that a scan plane supplying the most effective data for a target ultrasound examination coincides with the reference scan plane in the x-z plane in FIG. 3B. The B mode data acquired on both the reference scan plane and the auxiliary scan plane perpendicular to the reference scan plane are serially stored in the 2-D data memory unit 5.

The sub-volume data generating unit 6 includes a B mode data memory unit, an interpolation processing unit and a volume data memory unit. These units are not shown in FIG. 1. In the B mode data memory unit in the sub-volume data generating unit 6, B mode data are generated in the reception signals processing unit 4 based on reception signals collected by a volume scan on each of the plurality of 3-D sub-regions that are set on a diagnosis object portion in an object with accompanying to data of ultrasound transmission/reception directions. The interpolation processing unit in the sub-volume data generating unit 6 forms 3-D data by arranging the plurality of B mode data of 3-D sub-regions at a prescribed time phase, read out from the B mode data memory unit in accordance with the transmission/reception directions. The interpolation processing unit further generates sub-volume data formed of equidistant voxels by interpolating unequal distance voxels constructing the 3-D data. The acquired sub-volume data are stored in the volume data memory unit according to 3-D sub-region and also according to cardiac cycle time phase.

The sub-volume data composing unit 7 includes a memory circuit and a calculation circuit (not shown). The calculation circuit in the sub-volume data composing unit 7 composes the sub-volume data already stored in the memory circuit in the sub-volume data generating unit 6 as well as sub-volume data newly supplied from the sub-volume data generating unit 6 based on the accompanying 3-D sub-region data and cardiac cycle time phase data. The composed sub-volume data are stored in the memory circuit in the sub-volume data composing unit 7. While the sub-volume data newly supplied from the sub-volume data generating unit 6 has already included the composed sub-volume data stored in the memory circuit in the sub-volume data composing unit 7 as a sub-volume data acquired from the same 3-D sub-region, the calculation circuit updates the composed sub-volume data by replacing old stored sub-volume data with newly supplied sub-volume data. Sub-volume data will be explained later in detail.

The image data generating unit 8 includes a 2-D image data generating unit 81 and a 3-D image data generating unit 82. In a pre-scan mode, the 2-D image data generating unit 81 generates 2-D image data by arranging 2-D data on a reference scan plane and an auxiliary scan plane supplied from the 2-D data memory unit 5, corresponding to the accompanying data of ultrasound transmission/reception directions. If necessary, the 2-D image data generating unit 81 generates the 2-D image data by executing image processing, such as contour extraction or smoothing. Further, in a triggered entire volume mode, the 2-D image data generating unit 81 generates two MPR image data sets by reading out the composed sub-volume data stored in the memory circuit in the sub-volume data composing unit 7 and extracting voxels corresponding to the reference scan plane and an auxiliary scan plane among the composed sub-volume data.

The 3-D image data generating unit 82 is capable of generating 3-D image data such as volume rendering image data or surface rendering image data by performing a rendering process on the composed sub-volume data supplied from the sub-volume data composing unit 7. For instance, the 3-D image data generating unit 82 includes an opacity/color tone setting unit and a rendering process unit. The opacity/color tone setting unit in the 3-D image data generating unit 82 sets an opacity and a color tone for each voxel based on a voxel value from the composed sub-volume data. The rendering processing unit in the 3-D image data generating unit 82 generates 3-D image data by rendering the composed sub-volume data based on the opacity data or the color tone data set by the opacity/color tone setting unit.

The display unit 9 includes a display data generating unit, a data converting unit and a monitor. In a pre-scan mode, the display data generating unit generates display data by arranging 2-D image data generated on a reference scan plane and an auxiliary scan plane in the 2-D image data generating unit 81 and in the image data generating unit 8 in parallel. In a triggered entire volume mode, the display data generating unit generates display data by arranging, in parallel, MPR image data at a reference scan plane and an auxiliary scan plane of the composed sub-volume data generated in the 2-D image data generating unit 81 in the image data generating unit 8. The data converting unit performs D/A conversion and display format conversion of display data generated by the display data generating unit in order to display this data on the monitor.

FIG. 4A illustrates a reference scan plane and an auxiliary scan plane that are set in a pre-scan mode. As shown in FIG. 4A, the reference scan plane Sp1 is set in an azimuth direction so as to pass the z-axis of the ultrasound probe 3 at its center. The auxiliary scan plane Sp2 is set so as to orthogonally intersect the reference scan plane Sp1 in an elevation direction at the center axis. FIG. 4B is a display example of a 2-D image data Id1 acquired at the reference scan plane Sp1 and displayed on the display unit 9. FIG. 4C is a display example of a 2-D image data Id2 acquired at the auxiliary scan plane Sp2 and displayed on the display unit 9. Based on the two sets of 2-D image data acquired at the reference scan plane Sp1 and the auxiliary scan plane Sp2, a volume scan region for a triggered entire volume mode is set.

Thus, the position and direction of the ultrasound probe 3 is adjusted so that the reference scan plane Sp1 becomes the most effective scanning plane for acquiring the most effective data for a diagnosis of a target portion. By deciding the reference scan plane Sp1, the auxiliary scan plane Sp2 is also decided so as to orthogonally intersect the reference scan plane Sp1. Based on an azimuth scan scope R1 of the 2-D image data Id1 and an elevation scan scope R2 of the 2-D image data Id2 that are respectively acquired on the reference scan plane Sp1 and the auxiliary scan plane Sp2 and displayed on the display unit 9A in a pre-scan mode, a volume scan region S0 (FIG. 5) in a triggered entire volume mode is determined.

In a triggered entire volume mode, two MPR image data sets are also generated on the reference scan plane and the auxiliary scan plane in order to display composed sub-volume data on the display unit 9 as explained later.

The input unit 10 (FIG. 1) includes a display panel and an input device on an operation panel. An input device such as a keyboard, trackball, mouse, selection buttons, or input buttons may be used. By using the display panel and the input devices, various input operations and setting operations, such as inputting object data, selecting a pre-scan mode or a triggered entire volume mode, setting volume data generating conditions, setting generating conditions and/or displaying conditions of 2-D image data, MPR image data and 3-D image data, and inputting various command signals can be performed.

The input unit 10 includes a reference scan plane setting unit 101 for setting a reference scan plane, a volume scan region setting unit 102 for setting a volume scan region in a triggered entire volume mode based on 2-D image data acquired on the reference scan plane Sp1 and the auxiliary scan plane Sp2, and a sub-region interval setting unit 103 for setting a space interval between two sub-regions.

The sub-region setting unit 11 sets a plurality of 3-D sub-regions by dividing a volume scan region in a triggered entire volume mode (set by the volume scan region setting unit 102) on a diagnosis object portion based on the reference scan plane Sp1 data as well as volume scan region data and sub-region interval data at a prescribed sub-region space interval in a vertical direction to the reference scan plane. The reference scan plane Sp1 data and the volume scan region data are supplied from the reference scan plane setting unit 101 and the volume scan region setting unit 102 in the input unit 10 through the system controller 15. The sub-region interval data are supplied from the sub-region interval setting unit 103 through the system controller 15. The sub-region setting unit 11 further searches a 3-D sub-region including a reference scan plane among the set plurality of 3-D sub-regions.

The scan control unit 12 controls delay times of the transmission/reception unit 2 in order to perform 2-D scans on the reference scan plane and the auxiliary scan plane decided in a pre-scan mode on a diagnosis object portion, and also to perform a volume scan for each of the plurality of 3-D sub-regions set on the diagnosis object portion for a triggered entire volume mode. In order to perform volume scans in a triggered entire volume mode on each of the plurality of 3-D sub-regions that is set on a vertical (azimuth) direction to the reference scan plane, it is noted that initially, a volume scan is performed upon a particular 3-D sub-region including the reference scan plane, based on a retrieval result supplied from the sub-regions setting unit 11. Following this initial volume scan, a volume scan along the azimuth direction is performed upon a 3-D sub-region adjoining the initial 3-D sub-region. Doing so, a plurality of 3-D sub-region scans are performed in the triggered entire volume mode.

With reference FIGS. 5 and 6, setting a plurality of 3-D sub-regions in a volume scan region, and MPR image data acquisition of the particular 3-D sub-region including the reference scan plane are explained in detail. As illustrated in a non-limiting fashion in FIG. 5, in a pre-scan mode, the sub-region setting unit 11 sets four 3-D sub-regions S1-S4 on a volume scan region S0 along the elevation scan scope R2 based on two 2-D image data sets acquired on the reference scan plane and the auxiliary scan plane. The volume scan region S0, as illustrated in FIGS. 4B and 4C, is determined based on both of the azimuth scan scope R1 set in the 2-D image data Id1 on the reference scan plane Sp1 and the elevation scan scope R2 set in the 2-D image data Id2 of the auxiliary scan plane Sp2. The four of 3-D sub-regions S1 to S4 are formed by dividing the volume scan region S0 with a prescribed sub-region interval ΔR along the elevation direction to the reference scan plane.

FIG. 6A illustrates that the reference scan plane Sp1 is included in 3-D sub-region S3 among the four 3-D sub-regions S1 to S4. Thus, the 3-D sub-region S3 including the reference scan plane Sp1 becomes a particular 3-D sub-region among the four of 3-D sub-regions S1 to S4. A volume scan of this particular 3-D sub-region S3 is initially performed and acquired as sub-volume data Vd3, taking preference over the remaining three 3-D sub-regions S1, S2 and S4. Based on the sub-volume data Vd3 acquired, as illustrated in FIGS. 6B and 6C, MPR image data Im1 are generated from the reference scanning plane and Im2 is generated from the auxiliary scan plane in the sub-volume data.

FIG. 6B illustrates an example of an MPR image data Im1 generated by extracting a voxel of the reference scan plane at the acquired sub-volume data Vd3. FIG. 6C illustrates an example of MPR image data Im2 generated by extracting a voxel of the auxiliary scan plane at the acquired sub-volume data Vd3. During a prescribed period, for instance, one heart beat cycle, the acquired MPR image data Im1 and Im2 are displayed on a monitor in the display unit 9 in real time as video. In this instance, the MPR image data Im2 shown in FIG. 6B includes only a quarter (¼) of the image data of the scan scope along the elevation direction of the volume scan region.

Following the collection of sub-volume data for the particular 3-D sub-region S3, serial collections and compositions of sub-volume data for the respective 3-D sub-regions S4, S1 and S2 along the elevation direction will be explained with reference to FIGS. 7A through 7C.

FIG. 7A illustrates an example of electrocardiogram (ECG) waves in order to set heart beat cycles based on R wave measuring times t0, t1, t2, - - - tn in the ECG waves of an object by starting at an exchanging time ST from the pre-scan mode to the triggered entire volume mode. FIG. 7B illustrates examples of newly acquired and stored sub-volume data in each of the heart beat cycles. FIG. 7C illustrates examples of composed sub-volume data generated by composing the newly acquired and stored sub-volume data in each of the heart beat cycles with the already acquired and stored sub-volume data.

Just after exchanging from a pre-scan mode to a triggered entire volume mode at the time ST, the sub-volume data Vd31 for the 3-D sub-region S3 are acquired in a first heart beat (H.B.) period [t0-t1] in preference. By receiving the sub-volume data Vd31, the sub-volume data composing unit 7 stores the acquired sub-volume data Vd31 with both 3-D sub-region data and cardiac cycle phase data, for instance, an elapsed time of R waves, as accompanying data in a memory circuit. The sub-volume data composing unit 7 further supplies the acquired sub-volume data Vd31 to the 2-D image data generating unit 81 in the image data generating unit 8. The 2-D image data generating unit 81 generates MPR image data at the reference scan plane in the sub-volume data Vd3 and MPR image data at the auxiliary. The two generated MPR image data sets are displayed on a display unit 9 in real time.

Following the first heart beat (H.B.) period [t0-t1], in a second H.B. period [t1-t2], sub-volume data Vd41 for the 3-D sub-region S4 is acquired. The sub-volume data composing unit 7 composes the newly acquired sub-volume data Vd41 with the previous sub-volume data Vd31 stored in the memory circuit based on the accompanying 3-D sub-region data and cardiac cycle phase data. The 2-D image data generating unit 81 generates MPR image data of the composed sub-volume data at the reference scan plane and MPR image data of the obtained composed sub-volume data at the auxiliary scan plane and displays it on the display unit 9.

Similarly, in a third H.B. period [t2-t3], MPR image data are generated and displayed based on newly composed 3-D sub-volume data in which sub-volume data Vd11 acquired from the sub-region S1 are added. In a fourth H.B. period [t3-t4], sub-volume data Vd21 acquired from the 3-D sub-region S2 are newly added and generated for newly composed volume data, i.e., a volume data for the volume scan region. Using the composed volume data, MPR image data for the volume scan region are generated and displayed.

Following to the fourth H.B. period [t3-t4], in a subsequent fifth H.B. period [t4-t5], the sub-volume data composing unit 7 replaces the sub-volume data Vd31 in the composed sub-volume data 3-D sub-region S3 with newly acquired sub-volume data Vd32. Similarly, in each of the following sixth H.B. period [t5-t6], a seventh H.B. period, a eighth H.B. period [t6-t7], a ninth H.B. period [t7-t8] - - -, the sub-volume data of Vd41, Vd11, Vd21, - - -, are replaced by each of newly acquired sub-volume data of Vd42, Vd12, Vd22, - - - from the 3-D sub-regions S4, S1, S2, - - - , respectively. Thus, the composed sub-volume data are successively renewed by newly acquired sub-volume data. Based on renewed composed sub-volume data, MPR image data at the reference scan plane and the auxiliary scan plane is generated and displayed on the monitor.

FIGS. 8A-8D illustrate examples of displays of MPR image data Im1 on the reference scan plane and MPR image data Im2 on the auxiliary scan plane in the starting four H.B. periods from the first H.B. period [t0-t1] to the fourth H.B. period [t3-t4]. As illustrated in FIGS. 8A-8D, the MPR image data Im1 based on the sub-volume data Vd31 that is acquired in the first H.B. period [t0-t1] are repeatedly displayed as the same MPR image data Im1 in each of the following periods from the second H.B. period [t1-t2] to the fourth H.B. period [t3-t4]. After the fourth H.B. period [t3-t4], similarly an MPR image data Im1, based on sub-volume data Vd32 acquired in the fifth H.B. period [t4-t5], are repeatedly displayed from the fifth H.B. period [t4-t5] to the eighth H.B. period [t7-t8]. Similar displays of MPR image data Im1 are repeated after the ninth H.B. period [t8-t9].

In contrast, MPR image data Im2 on the auxiliary scan plane, as illustrated in FIGS. 8A to 8D, is updated in a different fashion. An image display of a first set of MPR image data Im2*a* on the auxiliary scan plane is acquired in the first H.B. period [t0-t1]. A second set of MPR image data Im2*b* on the auxiliary scan plane is acquired in the second H.B. period [t1-t2] and added to the first set of MPR image data. Next, an image display of a third MPR image data set Im2*c* on the auxiliary scan plane acquired in the third H.B. period [t2-t3] is added to the first and second MPR image data set Im2. Similarly, an image display of a fourth MPR image data Im2*d* on the auxiliary scan plane acquired in the fourth H.B. period [t3-t4] is added to the first and third MPR image data set Im2. After a fifth H.B. period [t4-t5], an image display of the MPR image data set Im2 on the auxiliary scan plane is successively replaced by a ¼ MPR image data set based on a newly acquired sub-volume data.

Turning to FIG. 1, the electro-cardiograph unit 13 measures heart beat cycles of an object. The electrocardiograph unit 13 includes measuring electrodes that detect cardiac waves by attaching, on the body surface of the object, an amplification circuit for amplifying the detected cardiac waves to a prescribed amplitude, and an A/D converter for converting the amplified cardiac waves to digital signals.

The cardiac cycle time phase calculating unit 14 calculates cardiac cycle time phases based on the cardiac waves supplied from the electrocardiograph unit 13. At first, the positions of R waves are detected by measuring a peak value of the cardiac waves. Next, a cardiac cycle time phase is calculated by determining the interval between two adjoining R waves (R-R interval) within a prescribed time interval. The calculated cardiac cycle time phase is affixed to the sub-volume data generated in the sub-volume data generating unit 6 as accompanying data.

The system control unit 15 includes a central processing unit (CPU) and a memory circuit. The above-mentioned various data inputted and set by the input unit 10 are stored in the memory circuit of the system control unit 15. The CPU of the system control unit 15 controls each unit in the ultrasound diagnosis apparatus 100 based on the inputted and set data in order to generate 2-D image data on the reference scan plane and the auxiliary scan plane set on a diagnosis object portion, to set a volume scan region based on the 2-D image data, to set 3-D sub-regions of the volume scan region, and to collect and compose sub-volume data on the 3-D sub-regions. Further, the CPU of the system control unit 15 controls the generation and display of the MPR image data of composed sub-volume data acquired on the reference scan plane and the auxiliary scan plane.

Figure 9:
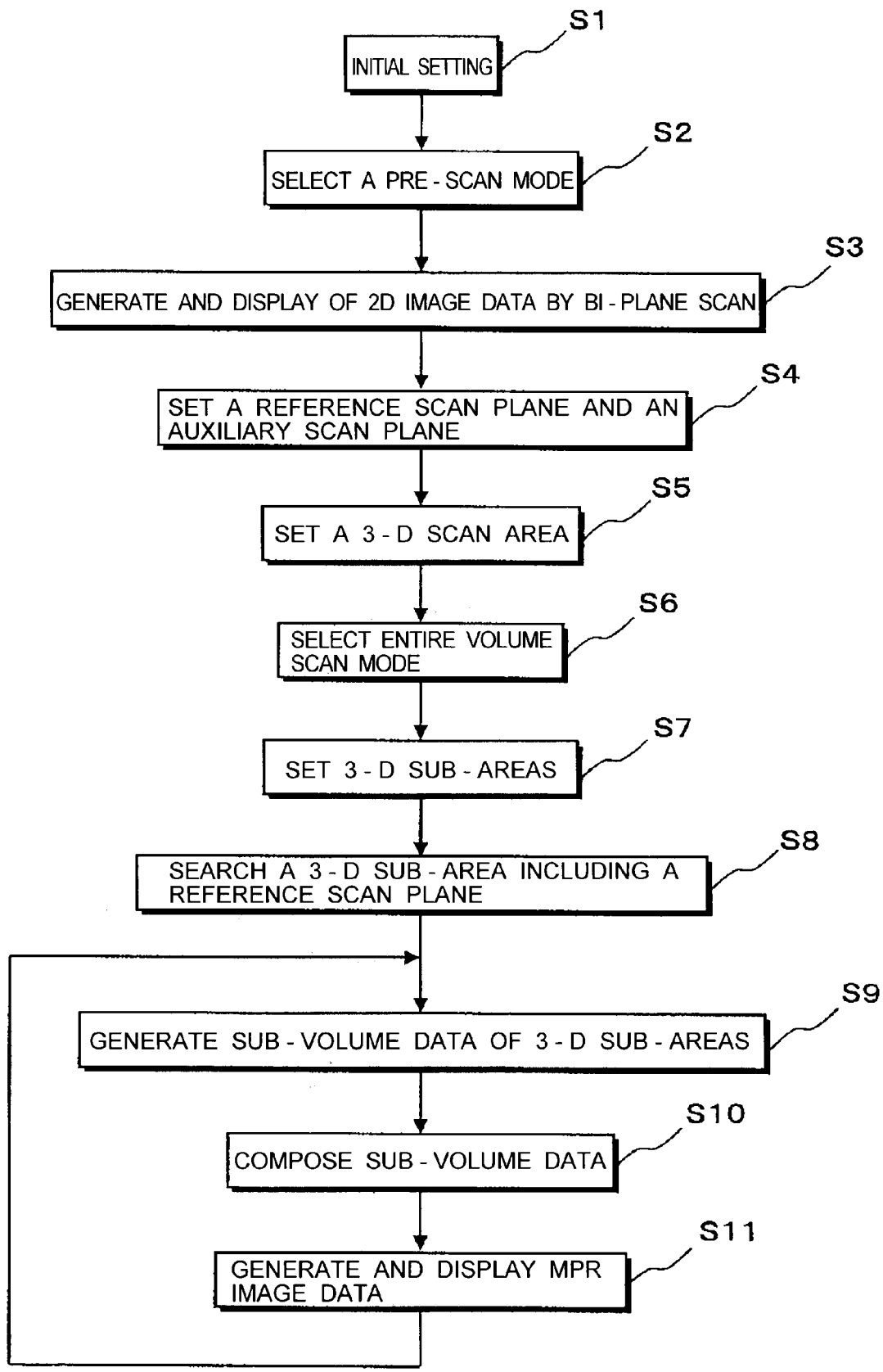
FIG. 9 is a flowchart illustrating processes for both the generation and display of MPR image data in the present embodiment.

FIG. 9 is a flowchart illustrating a process of generation and display of MPR image data for monitoring sub-volume data acquired from a plurality of 3-D sub-regions that are set on a diagnosis object portion in an object.

Prior to a pre-scan for setting a volume scan region and a reference scan plane of a diagnosis object portion, an operator of the ultrasound diagnosis apparatus 100 inputs object data, and sets various generating conditions, such as volume data, 2-D image data, MPR image data and 3-D image data through the input unit 10. Display conditions and sub-region intervals of the 3-D sub-regions are also set though the input unit 10. These inputted data and settings are stored in the memory circuit in the system control unit 15 (FIG. 9, step S1).

When the initial sets are completed, the operator selects a pre-scan mode coinciding with a bi-plane scan through the input unit 10 (FIG. 9, step S2). Then, an image data generation start command is inputted through the input unit 10, coinciding with attaching a tip portion of the ultrasound probe 3 on an appropriate position on an object. By supplying these command signals to the system control unit 15, generation and display of 2-D image data from the bi-plane scan is started (FIG. 9, step S3).

Observing two 2-D image data sets generated by the bi-plane scan and displayed on the display unit 9, the operator sets a scan plane that can acquire 2-D image data, including the most effective diagnosis data, as a reference scan plane and sets another scan plane orthogonal to the reference scan plane as an auxiliary scan plane through the reference scan plane setting unit 101 in the input unit 10 (FIG. 9, step S4).

Next, the operator sets a volume scan region, in a triggered entire volume mode, on the 2-D image data acquired on the reference scan plane and the auxiliary scan plane by using the volume scan region setting unit 102 in the input unit 10 (FIG. 9, step S5).

Observing the 2-D image data on the reference scan plane and the auxiliary scan plane displayed on the display unit 9, the operator adjusts the positions and directions of the ultrasound probe 3 so as to locate the reference scan plane at the most desired diagnosis portion. After adjusting the ultrasound probe 3 on the desired reference scan plane, a selecting instruction signal for the triggered entire volume mode is inputted through the input unit 10 (FIG. 9, step S6).

When the sub-region setting unit 11 receives the selecting instruction signals from the input unit 10 through the system control unit 15, it sets a plurality of 3-D sub-regions by dividing the 3-D scan region that is set on a diagnosis portion of an object by the volume scan region setting unit 102 with a prescribed sub-region interval along directions vertical to the reference scan plane, based on each of the reference scan plane data, volume scan region data and sub-region interval data, each supplied from the reference scan plane setting unit 101, the volume scan region setting unit 102 and the sub-region interval setting unit 103 in the input unit 10 (FIG. 9, step S7).

With reference to FIGS. 6 and 7, the following processes are explained. These processes include: a searching of a 3-D sub-region including the reference scan plane (FIG. 9, step S8), collection of sub-volume data at a plurality of 3-D sub-regions set to the volume scan region (FIG. 9, step S9), composition of a plurality of sub-volume data acquired at the plurality of 3-D sub-regions (FIG. 9, step S10), and generation and display of MPR image data of the composed sub-volume data on the reference scan plane and the auxiliary scan plane (FIG. 9, step S11).

In the above-mentioned step S7, the sub-region setting unit 11 that has set a plurality of 3-D sub-regions S1 to S4 of the volume scan region of an object searches the 3-D sub-region S3 including the reference scan plane among these 3-D sub-regions based on position coordinate data and supplies a searching result to the scan control unit 12 (FIG. 9, step S8).

The scan control unit 12 performs a volume scan of the 3-D sub-region S3, including the reference scan plane in the first H.B. period [t0-t1] that follows to the timing ST exchanging into a triggered entire volume mode. The sub-volume data generating unit 6 generates the sub-volume data Vd31 based on the acquired signals (FIG. 9, step S9).

The sub-volume data composing unit 7 stores the generated sub-volume data Vd31 with accompanying cardiac cycle phase data and 3-D sub-region data in its memory circuit and supplies the sub-volume data Vd31 to the 2-D image data generating unit 81 in the image data generating unit 8. The 2-D image data generating unit 81 generates MPR image data of the sub-volume data Vd31 supplied from the sub-volume data composing unit 7 synchronously on both the reference scan plane and the auxiliary scan plane. The generated MPR image data are displayed on the display unit 9 (FIG. 9, step S11).

In the second H.B. period [t1-t2] following the first H.B. period [t0-t1], the scan control unit 12 performs a volume scan of the 3-D sub-region S4 adjoining the 3-D sub-region S3. The sub-volume data generating unit 6 generates new sub-volume data Vd41 based on the acquired signals (FIG. 9, step S9).

The sub-volume data composing unit 7 composes the new sub-volume data Vd41 supplied from the sub-volume data generating unit 6 with the sub-volume data Vd31 stored in the memory circuit based on the cardiac cycle phase data and 3-D sub-region data. The composed sub-volume data is supplied to the 2-D image data generating unit 81 (FIG. 9, step S10).

Next, the 2-D image data generating unit 81 generates MPR image data of the composed sub-volume data on the reference scan plane and auxiliary scan plane supplied from the sub-volume data composing unit 7 and displays it on the display unit 9 (FIG. 9, step S11).

Similarly, in the third H.B. period [t2-t3], MPR image data on the reference scan plane and auxiliary scan plane are generated and displayed based on the composed sub-volume data that is added to the sub-volume data Vd11 acquired from 3-D sub-region S1 (FIG. 9, steps S9-S11).

In the fourth H.B. period [t3-t4], MPR image data on the reference scan plane and auxiliary scan plane, are generated and displayed based on the composed volume data being newly added the sub-volume data Vd21 acquired from the 3-D sub-region S2 reference scan (FIG. 9, steps S9-S11).

Further, in the fifth H.B. period [t4-t5] following the fourth H.B. period [t3-t4], the sub-volume data composing unit 7 renews the sub-volume data Vd31 which includes the composed sub-volume data with sub-volume data Vd32 acquired from the 3-D sub-region S3. In each of the following H.B. periods [t5-t6], [t6-t7], [t7-t8], - - - , sub-volume data Vd41, Vd11, Vd21, - - - formed of the respectively composed sub-volume data, are successively renewed by each of sub-volume data Vd42, Vd12, Vd22, - - - acquired from each of the 3-D sub-regions S4, S1, S2. Based on the renewed composed sub-volume data, MPR image data on the reference scan plane and the auxiliary scan plane is generated and displayed (FIG. 9, steps S9-S11).

Figure 10B:
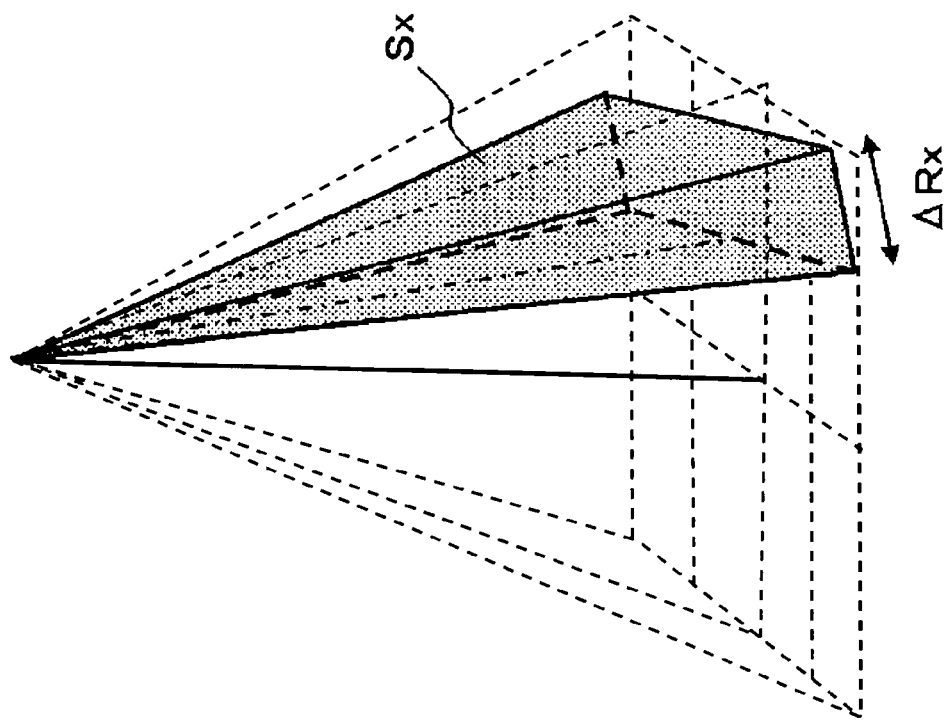
FIG. 10B illustrates a volume scan region being set based on the reference scanning plane shown in FIG. 10A.
Figure 10A:
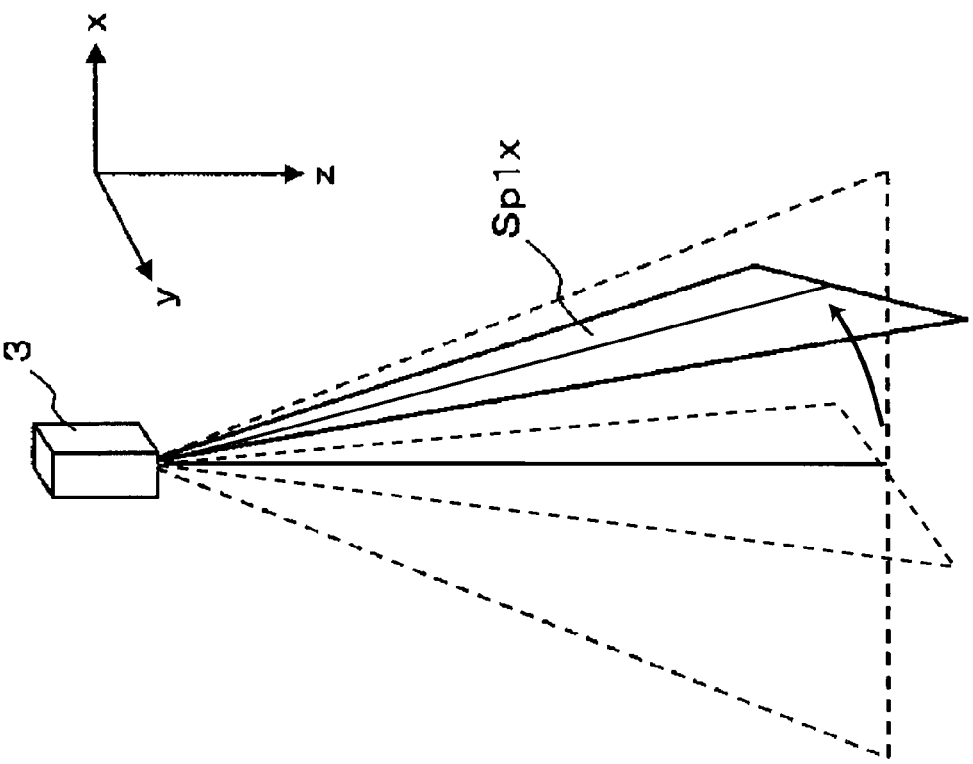
FIG. 10A illustrates another embodiment for setting a reference scanning plane in an arbitrary direction during the pre-scan mode.

FIGS. 10A and 10B illustrate another embodiment of the 3-D data acquiring method according to the present invention. In the above-mentioned embodiment, the MPR image data on the reference scan plane and the auxiliary scan plane of the volume scan region are generated by applying the heart beat synchronized (triggered) volume scan method on a plurality of 3-D sub-regions based on the reference scan plane and the volume scan region determined on a diagnosis object portion of an object. In this embodiment, as shown in FIG. 10A, the reference scan plane Sp1x is arbitrarily rotated and moved from the z-axis of an ultrasound probe 3 along an azimuth direction. As shown in FIG. 10A, based on the reference scan plane Sp1x, a 3-D scan region Sx having a prescribed region width ΔRx is set on a diagnosis object portion of an object. MPR image data are generated based on volume data acquired from the 3-D scan region Sx on the reference scan plane and auxiliary scan plane.

As mentioned above, FIG. 10A illustrates a reference scan plane Sp1x set in an arbitrary direction in a pre-scan mode. FIG. 10B illustrates a 3-D scan region Sx having a prescribed region width ΔRx that is set on a diagnosis portion based on the reference scan plane Sp1x. In this case, the 3-D scan region Sx is set such that the edge surface of the 3-D scan region Sx coincides to the reference scan plane Sp1x. When MPR image data are generated and displayed by moving a scan plane that is set to the 3-D scan region Sx along a direction vertical to the reference scan plane a display is performed in preference. On the other hand, generation of MPR image data on the reference scan plane is performed in preference to generation of MPR image data on another scan plane. By doing so, it becomes possible to continuously observe both the 2-D image data on the reference scan plane and MPR image data on the reference scan plane in the triggered entire volume mode.

According to the present embodiment, MPR image data on the scan plane are generated and displayed by moving the scan plane included in a 3-D (volume) scan region in a vertical direction to the reference scan plane. In this case, it becomes possible to continuously observe both 2-D image data on the reference scan plane and MPR image data on the reference scan plane in the triggered entire volume mode by performing generation of MPR image data on the reference scan plane in preference to generation of MPR image data on another scan plane.

As explained above, according to the present invention, when volume data are collected in a wide scope by applying a triggered (heart beat synchronized) volume scan method from a plurality of 3-D sub-regions set on a diagnosis object portion of an object, it becomes possible to continuously observe both 2-D image data on the reference scan plane and MPR image data on the reference scan plane in the triggered entire volume mode by performing generation of MPR image data on the reference scan plane in preference to the generation of MPR image data on another scan plane. Consequently, it can increase monitoring accuracy due to increased accuracy of collected volume data. Further, it can reduce burdens for a monitoring operator.

According to the present invention, a reference scan plane and an auxiliary scan plane are set on a diagnosis object portion of an object. A volume scan region for a triggered entire volume mode is set based on 2-D image data acquired on these two scan planes. Consequently, it is possible to set the most effective volume scan region for a diagnosis. Further, according to the present invention, monitoring the volume data is performed based on the two MPR image data sets generated on the reference scan plane and auxiliary scan plane of the composed sub-volume data generated in the entire volume mode. Consequently, monitoring accuracy can be increased.

Figure 11B:
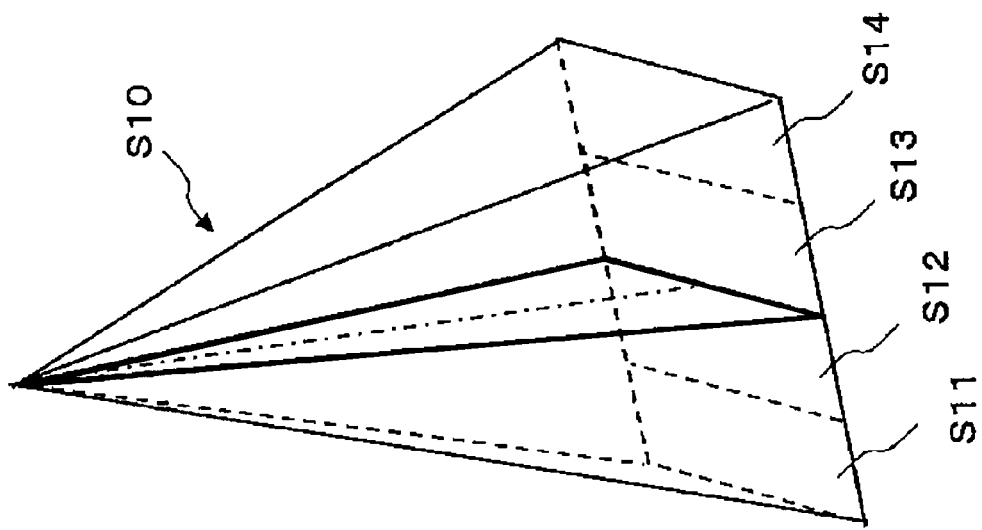
FIG. 11B illustrates another embodiment for setting a plurality of 3-D sub-regions by dividing based on an auxiliary scan plane perpendicularly intersecting the reference scanning plane shown in FIG. 11A.
Figure 11A:
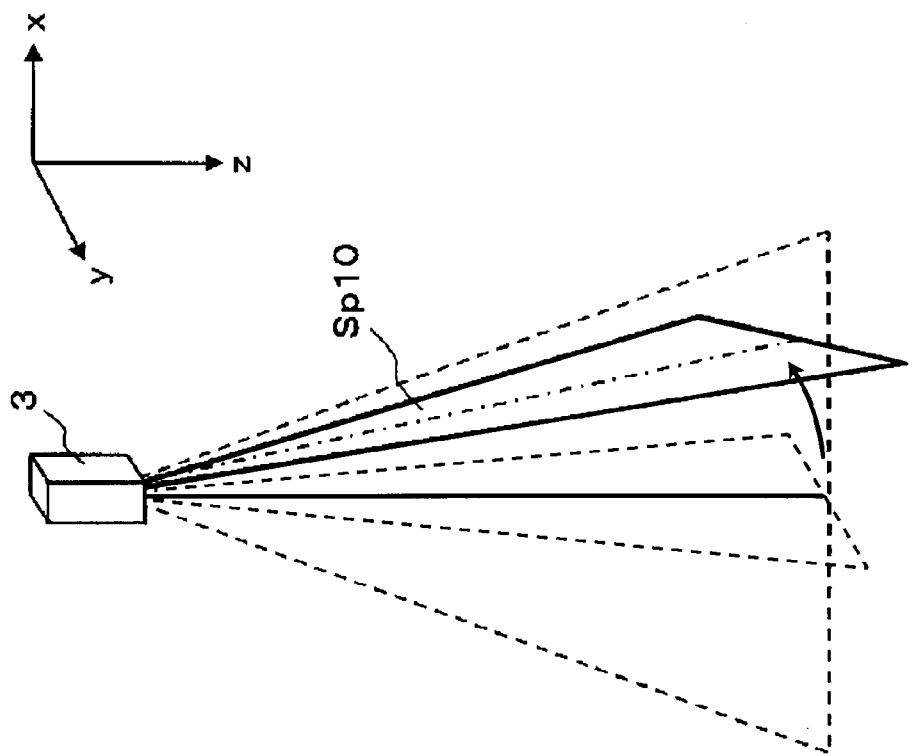
FIG. 11A illustrates another embodiment for setting a reference scanning plane in an arbitrary direction against the direction of the transducer array.

FIG. 11A illustrates another embodiment of a reference scan plane and an auxiliary scan plane. In this embodiment, a reference scan plane Sp10 is set by rotating the orientation of the transducers of ultrasound probe 3 in an arbitrary direction along an azimuth direction. In this embodiment, as illustrated in FIG. 11B, a volume scan region S10 in an entire volume mode is set based on the auxiliary scan plane orthogonal to the reference scan plane Sp10. Further, four 3-D sub-regions, S11 to S14, are set by dividing along an elevation direction.

In the above-mentioned embodiment, a reference scan plane and an auxiliary scan plane are orthogonally intersected. In so far as 3-D data are acquired, such an orthogonal intersection is not an inevitable feature. It is possible to intersect both planes with a prescribed angle that is nonorthogonal. Further, if a pre-scan mode is performed by multi-plane scan of more than three scan planes, it is possible to set more than two scan planes as auxiliary scan planes.

In the above-mentioned embodiment, it is mentioned that sub-volume data are collected on a reference scan plane in a volume scan region. However, if it is difficult to acquire the sub-volume data on the reference scan plane, it may be necessary to generate MPR image data by using sub-volume data collected on the closest 3-D sub-region to the reference scan plane. This is also an important feature of this invention.

In the above-mentioned embodiment, MPR image data in a triggered entire volume mode are collected on a reference scan plane and an auxiliary scan plane that are set in a pre-scan mode. It is possible to move a scan plane for collecting MPR image data from the reference scan plane to another scan plane.

In the above-mentioned embodiment, 2-D image data in a pre-scan mode, and volume data including MPR image data and 3-D image data in a triggered entire volume mode are generated based on B mode data. Of course, it is possible to generate these data based on another ultrasound data, such as color Doppler data.

In the above-mentioned embodiment, as an exemplary feature, a volume scan region S0 is comprised of four 3-D sub-regions S1 to S4 and a reference scan plane is included in a third 3-D sub-region S3. It is noted that the number of the 3-D sub-regions and location of the 3-D sub-region including the reference scan plane are not limited as mentioned in the embodiment.

In the above-mentioned embodiments, a plurality of 3-D sub-regions are set up in a vertical direction to a reference scan plane. Of course, it is possible to set the plurality of 3-D sub-regions by rotating the reference scan plane around the z-axis of an ultrasound probe in a prescribed angle.

Other embodiments consistent with the present invention will be apparent to those skilled in the art from consideration of the specification and practice of the present invention disclosed herein. It is intended that the specification and examples be considered as exemplary only, with the true scope and spirit of the present invention being indicated by the following claims.

What is claimed is:

1. An ultrasound diagnosis apparatus configured to sequentially acquire volume data by performing a 3D scan through transmitted ultrasounds on a diagnosis object portion in an object, the ultrasound diagnosis apparatus comprising:
    a 2-D image data generating unit configured to sequentially generate 2-D image data based on receiving signals collected by performing a 2D scan of a pre-scan mode to a reference scanning plane for the diagnosis object portion;
    a scan control unit configured to sequentially scan a plurality of 3D sub-regions formed by dividing the 3D scan region of a real imaging mode along a prescribed direction, and to perform a 3D scan on the 3D sub-region that contains at least a part of the reference scanning plane prior to performing 3D scans on another 3D sub-region, when the imaging mode transfers from the pre-scan mode to the real imaging mode; and
    a display unit configured to display the image data acquired through the ultrasound scans by the scan control unit.

2. The ultrasound diagnosis apparatus according to claim 1, further comprising:
    a sub-region setting unit configured to set the plurality of 3D sub-regions by dividing the 3D scan region along a vertical direction to the reference scanning plane.

3. The ultrasound diagnosis apparatus according to claim 1, further comprising a planar image data generating unit configured to generate MPR image data for the reference scan plane based on sub-volume data acquired by the volume scan over the plurality of 3-D sub-regions, wherein the display unit displays the MPR image data for the reference scan plane generated in the real imaging mode by following a display of the 2D image data of the reference scanning plane generated in the pre-scan mode when the imaging mode transfers from the pre-scan mode to the real imaging mode.

4. The ultrasound diagnosis apparatus according to claim 1, further comprising:
    a sub-volume data compounding unit configured to generate the volume data by compounding sub-volume data acquired from the plurality of 3-D sub-regions; and
    a cardiac cycle phase calculating unit configured to calculate a cardiac cycle phase based on a cardiogram detected from the object,
    wherein the sub-volume data compounding unit is configured to generate the volume data by compounding a plurality of the sub-volume data based on the cardiac cycle phase.

5. The ultrasound diagnosis apparatus according to claim 1, further comprising:
    a volume scan region setting unit configured to set volume scan region based on the 2D image data generated by the 2D image data generating unit.

6. The ultrasound diagnosis apparatus according to claim 1, wherein a volume scan region setting unit is configured to set volume scan region based on the 2D image data generated on the reference scanning plane and on an auxiliary scan plane orthogonally crossing to the reference scanning plane.

7. The ultrasound diagnosis apparatus according to claim 1, further comprising:
    an ultrasound probe including 2D array transducers,
    wherein the reference scanning plane setting unit is configured to set the reference scanning plane along the array direction of the transducers.

* * * * *